US009074731B2

United States Patent
Barrett (10) Patent No.: US 9,074,731 B2
(45) Date of Patent: Jul. 7, 2015

(54) GAS MONITORING SYSTEM WITH OXYGEN CONTROL FOR HUMAN LIFE SUPPORT IN ENCLOSED REFUGE SPACES

(71) Applicant: VENTURE CORPORATION LIMITED, Singapore (SG)

(72) Inventor: James P. Barrett, Liberty Lake, WA (US)

(73) Assignee: VENTURE CORPORATION LIMITED, Singapore (SG)

( * ) Notice: Subject to any disclaimer, the term of this patent is extended or adjusted under 35 U.S.C. 154(b) by 0 days.

(21) Appl. No.: 13/717,559

(22) Filed: Dec. 17, 2012

(65) Prior Publication Data

US 2013/0153060 A1    Jun. 20, 2013

Related U.S. Application Data

(60) Provisional application No. 61/576,258, filed on Dec. 15, 2011.

(51) Int. Cl.
  *F17D 1/00* (2006.01)
(52) U.S. Cl.
  CPC .............. *F17D 1/00* (2013.01); *Y10T 137/8158* (2015.04); *Y02E 60/34* (2013.01)
(58) Field of Classification Search
  CPC ......... E21F 11/00; E04H 9/12; E04H 1/1277; E04H 9/00; E04H 9/04; A62B 31/00; A62B 13/00; A62B 11/00
  USPC .............. 73/23.2, 23.31, 31.05, 31.01–31.03, 73/23.21; 137/551
  See application file for complete search history.

(56) References Cited

U.S. PATENT DOCUMENTS

| | | | |
|---|---|---|---|
| 7,448,252 B2 * | 11/2008 | Brosnihan et al. | 73/31.03 |
| 2007/0113686 A1 * | 5/2007 | Desrochers et al. | 73/863.33 |
| 2007/0200420 A1 * | 8/2007 | McCormick | 299/95 |
| 2009/0316530 A1 * | 12/2009 | Bunyard et al. | 367/137 |
| 2010/0175334 A1 * | 7/2010 | McDonald et al. | 52/79.9 |
| 2011/0088339 A1 * | 4/2011 | McCarthy | 52/169.6 |
| 2011/0107681 A1 * | 5/2011 | Zhang | 52/2.17 |
| 2011/0318566 A1 * | 12/2011 | Miller et al. | 428/312.2 |
| 2012/0046792 A1 * | 2/2012 | Secor | 700/276 |

* cited by examiner

Primary Examiner — Daniel S Larkin
Assistant Examiner — Jamar Ray
(74) Attorney, Agent, or Firm — Craig M. Stainbrook; Stainbrook & Stainbrook, LLP (57) ABSTRACT

A gas monitoring and oxygen supply control system, including a flame-proof and explosion proof housing; a gas monitoring sensor system enclosed in said housing, said sensor system including a sensor controller, a plurality of gas sensors, and a CPU; air sampling pipes in fluid communication with said gas sensors and with the atmospheres to be sampled; input sampling ports disposed on said air sampling pipes and exposed to the atmospheres to be sampled; at least one exhaust pipe for venting gases to a select atmosphere outside said housing; flame-proof port assemblies disposed through a wall of said housing separating said sensor system from an outside atmosphere and through which said air sampling pipes and said exhaust pipe are disposed; at least one pump operatively connected to said air sampling pipes so as to provide both suction and exhaust, said pump electronically connected to and controlled by said CPU; a plurality of valves disposed on said air sampling pipes and electronically coupled to and controlled by said CPU; and a transceiver coupled to said CPU and to a feedthrough radio antenna disposed through a side of said housing for communicating bi-directionally with one or more handsets.

19 Claims, 5 Drawing Sheets

| Ref. No. | Feature |
|---|---|
| 20 | Pump |
| 22 | Valves |
| 24 | CPU |
| 26 | Ports |
| 28 | Packing glands |
| 30 | Explosion proof/ flame-proof ports |
| 32 | Exhaust orifices |
| 34 | Outside exhaust orifice |
| 36 | Calibration gasses |
| 38 | Radio |
| 42 | Feed through antennas |
| 44 | Oxygen air piloted release valve |
| 46 | Pump |
| 50 | Battery manager systems |
| 52 | Batteries |
| 56 | Power cable |
| 58 | Charge power source |

FIG. 1

| Ref. No. | Feature |
|---|---|
| 20 | Pump |
| 22 | Valves |
| 24 | CPU |
| 26 | Ports |
| 28 | Packing glands |
| 30 | Explosion proof/flame-proof ports |
| 32 | Exhaust orifices |
| 34 | Outside exhaust orifice |
| 36 | Calibration gasses |
| 38 | Radio |
| 42 | Feed through antennas |
| 44 | Oxygen air piloted release valve |
| 46 | Pump |
| 50 | Battery manager systems |
| 52 | Batteries |
| 56 | Power cable |
| 58 | Charge power source |

GAS MONITORING SYSTEM WITH OXYGEN CONTROL FOR HUMAN LIFE SUPPORT IN ENCLOSED REFUGE SPACES

CROSS REFERENCES TO RELATED APPLICATIONS

The present application claims the benefit of the filing date of U.S. Provisional Patent Application Ser. No. 61/576,258, filed Dec. 15, 2011 (Dec. 15, 2011).

SEQUENCE LISTING

Not applicable.

STATEMENT REGARDING FEDERALLY SPONSORED RESEARCH OR DEVELOPMENT

Not applicable.

THE NAMES OR PARTIES TO A JOINT RESEARCH AGREEMENT

Not applicable.

INCORPORATION BY REFERENCE OF MATERIAL SUBMITTED ON A COMPACT DISC

Not applicable.

BACKGROUND OF THE INVENTION

1. Field of the Invention

This invention relates to safety systems for miners operating in an underground mine. More particularly, this invention relates to a toxic gas removal and air conditioning system for providing safe and breathable air to occupants of a miner survival chamber when outside atmosphere contains potential harmful gases.

2. Background Discussion

Events such as floods, nuclear radiation accidents, explosions, fires, chemical spills, terrorist toxic gas attacks, and many other such hazards, can require that humans in the affected areas take refuge. Underground mines in particular present a host of such hazards. There are numerous risks inherent in underground mining operations: fires, cave-ins, methane or coal-dust explosions, flooding, asphyxiation, poisonous gasses in the mine atmosphere, and so forth.

When any person must seek refuge from an event such as those described above, most especially when miners are trapped underground, their survival may depend upon their ability to find temporary shelter inside a survival refuge chamber until the danger has passed, or until rescue responders find and extract the miners from the chamber. Specially designed survival chambers are typically placed at various locations in a mine, and miners are trained and drilled to know these locations. In this way, if a mine accident occurs, the miners can quickly find and enter the nearest survival chamber, and they can occupy the chamber until it is safe to exit.

Since survival chambers are air-sealed to prevent the intrusion of dangerous gases that may be present in the mine atmosphere outside the chamber, the miners have only four possible sources of oxygen (O2). These include:)1(the O2 that was present in air in the chamber before it was sealed, which can include O2 found in compressed air tanks inside the chamber; (2) the O2 that can be introduced into the chamber another source that is outside the chamber, including O2 found in (a) air piped into the chamber from outside compressed air tanks; (b) the mine atmosphere immediately surrounding the chamber; and (c) air piped into the chamber from a source outside the mine.

The amount of time that a miner (or group of miners) can survive in a survival chamber is dependant, at least in part, on the amount of O2 available inside the chamber. Since the rescue operations can take days (even weeks), it is critically important that survivable O2 levels be present in the air inside the chamber for the longest period of time possible.

It is important to recognize that the air inside a sealed chamber occupied by humans becomes contaminated over time, due primarily to the occupants' exhaling air that introduces waste gases, principally additional carbon dioxide ($CO_2$) into the chamber's atmosphere.

When the ratio of $CO_2$ to $O_2$ is too large, survival chamber occupants can suffer $CO_2$ poisoning. To prevent this condition, gas monitoring and air-scrubbing systems are employed within the chamber to remove excess $CO_2$ from the chamber atmosphere.

Any such system must be intrinsically safe in a mine environment. It must also be very rugged, due to the hostile environment characteristic of underground mines. Additionally, it must be capable of surviving the forces present inside the chamber when an explosion occurs outside the chamber. Such a system must also be intrinsically safe (that is, unable to generate unsafe conditions, such as generating a spark, or emitting an explosive or poisonous gas in sufficient quantity to present a danger).

Such a system would optimally detect any loss of externally-supplied power and automatically begin operation when such a condition is detected, so that it would not be necessary for miners to manually start or operate the air scrubber.

Further, the noise generated by a monitoring or scrubbing system should be minimized. This is because miners occupying the survival chamber have no choice but to listen to system noise for extended periods of time, and the adverse psychological impact of stress from long-term exposure to noise can be significant.

In order for a rescue team to verify that gas monitors and air-scrubbers are operating (without entering the survival chamber), the systems should have means to wirelessly communicate system conditions to communications and control systems outside the chamber.

In the solutions of known current art, there are no gas monitoring or air-scrubbing systems for use in survival chambers in underground mines that meet all of these requirements. There is thus an urgent and critical need for such a system to significantly improve the ability for miners trapped in a mine to survive.

BRIEF SUMMARY OF THE INVENTION

The present invention solves the foregoing problems by providing a suitable atmosphere for human occupants of an enclosed refuge chamber or space when they must seek refuge from catastrophic life-threatening event.

The principal advantages provided include intrinsic safety together with dramatically improved power efficiencies needed to achieve (1) practical amounts of self-contained battery energy storage, (2) low risk of hydrogen off-gassing with its attendant explosion risk, (3) low risk of explosion/ignition for a system used in an enclosed space where pure oxygen is used and dispensed, and (4) accurate automated measurements of atmospheric gases from three separate zones in/around an enclosed space occupied by humans who must rely upon those measurements to create and maintain a life supporting atmosphere.

The inventive gas monitoring system with oxygen control provides safe, accurate, and automated measurement of atmospheric conditions necessary to maintain human survivability. This is particularly important for human refuge chamber occupants who may be so injured or otherwise compromised by a mine accident as to be unable to manually operate alternative life-support systems. The promise of improved survivability from mine accidents will motivate widespread deployment of enclosed-space refuge shelters throughout the world in a host of hazardous areas, and will thereby save lives when major atmospheric accidents occur.

Accordingly, the inventive system provides a completely self-contained and automated gas monitoring system for gathering and testing gas samples from a number of different locations for the purpose of analyzing the breakdown component gases present in each sample. The system is principally intended for use in and around enclosed refuge chambers where humans must seek refuge from harmful atmospheres for several days when a catastrophic accident creates hazardous environmental conditions. Its use, however, is not limited to such circumstances or environments. The system has similar innovative usefulness in many other applications where gases must be continuously monitored and controlled, and is a practical solution to numerous other human life-support situations.

In addition to the automated reporting and data-logging of measurement results, which is a foundational feature of the system, the system includes a number of control functions in which actions are commanded or recommended by the system in response to certain alert/alarm/action thresholds being reached. One example is the automated release of oxygen via a control valve according to the sensed need to replenish oxygen as it is consumed by human refuge chamber occupants. This "oxygen control" is a closed-loop control system that operates by opening and closing an oxygen release valve on a compressed oxygen supply in response to a computer control signal so as to maintain the breathable oxygen percentage inside the refuge chamber to within the optimal 18.5-23% range required to sustain life (i.e. normal breathable air). A redundant signal is also provided to the refuge chamber occupants so that they are able to manually actuate an oxygen release valve in the event of a failure of the automated valve. The oxygen supply in the refuge chamber is otherwise depleted by the action of the humans breathing the enclosed air supply and consuming the oxygen in that air.

A novel intrinsically safe valve is used for the oxygen supply system that does not have a solenoid nor any wiring. This is because inductance in a solenoid valve is entirely prohibited due to intrinsic safety concerns, especially where pure oxygen is present and could be easily ignited by a spark or electrical heat. This valve is "air piloted," meaning it is actuated via a tiny compressed-air signal from a micro-pump inside the explosion-proof (XP) enclosure that houses the gas monitor and control electronics. The compressed air piloting signal is generated by a pump inside the XP enclosure, and is "sent" via a tiny tube that runs from the XP box across the length of the refuge chamber to the air piloted valve where it is situated with the oxygen supply tanks. Another example of a control function is the optional ability of the system to control carbon dioxide scrubbing and cooling/dehumidifying systems so as to maintain toxic $CO_2$ concentrations, heat and humidity buildup in an integrated enclosed life-support system.

The gas monitoring system of the present invention includes four sensor transducers and associated circuitry inside the XP enclosure, together with a set of valves and vacuum pumps used to deliver gas samples from various remote locations of concern. Air (gas) samples are drawn through long and very small diameter tubes from the various parts of the refuge chamber interior, as well as from atmosphere outside the chamber, and these air samples are presented to the sensors under automated computer control. All automated calibrations and measurements are carried out under the action of CPU control interacting with the various sensor circuits. The measurement results are presented to portable display units wirelessly via digital packet radios mated to the CPU inside the XP enclosure. The wireless signals are able to enter and exit the XP enclosure via novel RF feedthrough ports and passive antennas.

The air sampling ports require a sophisticated "explosion-proof/flame-proof port" that is designed to deal with the conflicting requirements of allowing air samples to get in (i.e. get into the XP enclosure) while disallowing a hydrogen/oxygen or methane/oxygen flame or explosion gas product from escaping the XP enclosure, should there be any malfunctioning of the electronics inside. An extensive hydrogen/oxygen and methane/oxygen explosion- and flame-test protocol was used with independent third party test labs to verify that the flame-proof port described herein performs properly under all of the worst-case conditions.

The present invention provides accurate measurements of gases in the harsh environment of mines where explosion and fire hazard, and the combustion gases produced cause great stress to the accuracy of conventional sensing systems. It samples several areas simultaneously and automatically using innovative flame-proof/explosion-proof air sampling ports and sampling tubes. It reports results wirelessly and also allows maintenance checks and calibrations to be performed wirelessly without any need to enter the refuge chamber. This invention is self-contained and lasts 96 hours in continuous operation while not requiring battery changes. It maintains batteries at the ready in a fully charged state in known explosive atmospheres where battery charging can be prohibitive by explosion risk. It is proven to be ignition safe and explosion-proof/flame-proof in enriched oxygen atmospheres where methane and/or hydrogen are present in worst-case concentrations. It is fully automated, which unburdens the human occupants who may be injured, confused, and/or exhausted and unable to maintain their own detailed task schedule.

The invention includes numerous alert/alarm threshold checks with annunciators to signal occupants with important information. It uses lead-acid batteries so small as not to contain enough water to create a hydrogen off-gassing hazard, even in a worst-case abuse or fault of the batteries, and even in a chamber lacking venting for hydrogen. No other known system provides provision for automated control of the oxygen release so as to automatically maintain breathable atmosphere where occupants are continually depleting oxygen through respiration.

Other objects, features, and advantages include:

It is a completely self-contained and automated gas monitoring system, able to operate safely for at least 96 hours on internal battery in places having explosive atmospheres such as methane and hydrogen, all without giving rise to an ignition hazard.

The system automates tasks that may otherwise be challenging for refuge chamber occupants who may have mental deficit from injury or accident prior to occupying a refuge chamber, or who may be poorly educated, or who may be overcome by panic or anxiety associated with underground mine accidents.

The system obviates the need for frequent manual battery changes, and operator interventions.

The system includes a state-of-the-art sensor subsystem consisting of electrochemical sensor transducers for carbon monoxide (CO) and oxygen ($O_2$), plus non-dispersive infrared transducers for methane ($CH_4$) and carbon dioxide ($CO_2$). These sensors are selected and combined to provide +/−10% accuracy of measurement where no such measurements were previously possible in mining, especially in the case of $CO_2$, where harsh environmental conditions exist along with other unusual challenges, such as high gas saturation (immediately after an accident but just before a purge) and cross-sensitivity to other gases.

The inventive system can sample/measure multiple remote areas with one single sensory subsystem.

The system includes novel RF feedthrough ports and passive antenna structures to transfer wireless energy across the metal barriers that would otherwise disallow propagation.

Still further, the system includes innovative small portable wireless handsets to allow roaming and convenient use by refuge chamber occupants.

Yet another feature is that the system provides completely wireless remote monitoring from the surface via MineTracer wireless mesh network or other suitable wireless sensor network (optional, if MineTracer network is installed, or if a MineTracer FASC is installed outside the chamber, as discussed further, below).

The system provides the ability to conduct completely wireless remote monitoring by walk-by inspection/maintenance personnel via a handheld wireless monitoring unit, thus eliminating the need to enter the tamper-proof sealed refuge chamber.

The system provides for completely wireless calibration management by walk-by inspection/maintenance personnel via the handheld wireless monitoring unit. No need to enter the tamper-sealed refuge chamber.

The system further includes intrinsically safe standby battery charging, plus explosion-proof/flame-proof enclosures for all non-intrinsically-safe battery powered electrical parts of the system. All non-intrinsically safe portions of the system are rendered safe for use in hazardous explosive atmospheres including methane and hydrogen mixtures with oxygen.

Next, the system uses innovative flame-proof and explosion-proof gas sampling ports that allow gas samples to be drawn/exhausted with small and efficient low-pressure pumps while at the same time disallowing worst-case hydrogen, methane, oxygen flames or explosive gas ejections.

Heat generation/dissipation of the system is carefully engineered to be at a absolute minimum to avoid adding heat to the occupied environment and to minimize the size of battery needed to power the system for 96 hours or more. This ensures that the lead-acid batteries used are so small as to not contain enough water ($H_2O$) to allow an explosive atmosphere to be formed by worst-case battery off-gassing of free hydrogen. This fail-safe guarantees against the need to ventilate hydrogen from the refuge chamber.

Innovative and cost-effective "packing glands" are employed to provide air-tight portals through which air sampling tubes and RF feedthrough can pass.

The system will start automatically without occupant intervention to ensure fail-safe startup for victims who may barely reach the chamber before succumbing to exhaustion or unconsciousness.

Control of the system is automated to provide oxygen to victims who may be injured or may have reduced ability to manage their own oxygen replenishment via manually operated oxygen release valves.

The system further employs an innovative air-piloted oxygen release valve and control system that is unequivocally safe against explosion hazard in enriched oxygen that may be present when there are faults with pressurized oxygen systems.

The system can be configured to send completely wireless instructions from the gas monitoring system to a separate MineTracer toxic gas scrubber and/or cooler so as to control the rate of toxic gas removal and cooling/dehumidifying with automated computer assistance. Other control system functions also possible for other associated systems (activate a pressure release valve for example if pressure exceeds a certain threshold within the refuge chamber).

The system is deployed in an extremely rugged explosion-proof and intrinsically safe designs suitable to withstand the secondary effects of a 15 psi explosion and flash fire outside of the refuge chamber as dictated in the MSHA test protocol for approved refuge chambers.

The system can be a standalone system, able to operate as a completely autonomous atmospheric monitoring system in a mine or any other target monitoring area independent from any association with any refuge chamber.

Control of the system is provided by innovative software and firmware algorithms that give the system intelligence for managing an enclosed space atmospheric life-support system.

The inventive system can provide self-health check results (of battery state for example), and can also monitor for such crucially important events as a pressurized oxygen tank failure, all via a wireless portable interface from outside of the refuge chamber. It also includes guardian functions built into the software and firmware to alert refuge occupants to potentially life threatening changes in atmospheric conditions.

Other novel features which are characteristic of the invention, as to organization and method of operation, together with further objects and advantages thereof will be better understood from the following description considered in connection with the accompanying drawings, in which preferred embodiments of the invention are illustrated by way of example. It is to be expressly understood, however, that the drawings are for illustration and description only and are not intended as a definition of the limits of the invention. The various features of novelty that characterize the invention are pointed out with particularity in the claims annexed to and forming part of this disclosure. The invention does not reside in any one of these features taken alone, but rather in the particular combination of all of its structures for the functions specified.

The foregoing summary broadly sets out the more important features of the present invention so that the detailed description that follows may be better understood, and so that the present contributions to the art may be better appreciated. There are additional features of the invention that will be described in the detailed description of the preferred embodiments of the invention which will form the subject matter of the claims set out in the non-provisional patent application claiming the benefit of the priority date of the instant application.

BRIEF DESCRIPTION OF SEVERAL VIEWS OF THE DRAWINGS

The invention will be better understood and objects other than those set forth above will become apparent when consideration is given to the following detailed description thereof. Such description makes reference to the annexed drawings wherein:

FIG. 1 is a block diagrammatic view of the gas monitoring system of the present invention, while

DETAILED DESCRIPTION OF THE INVENTION

Figure 1:
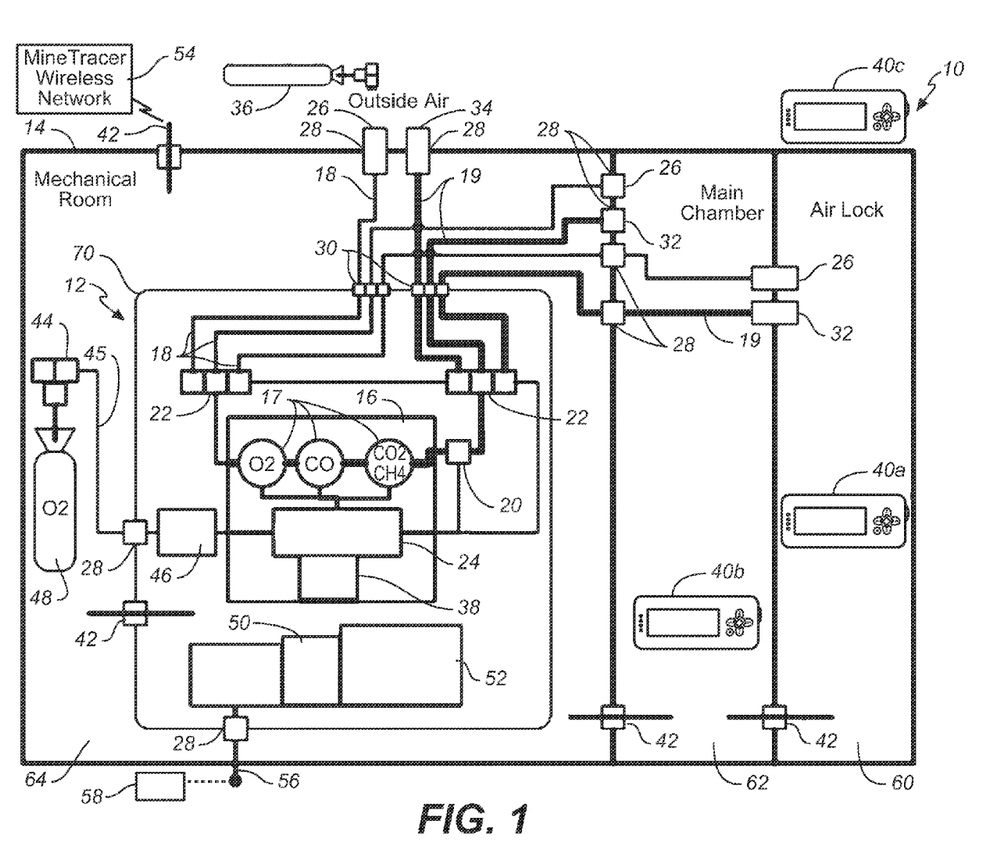
Figure 1A:
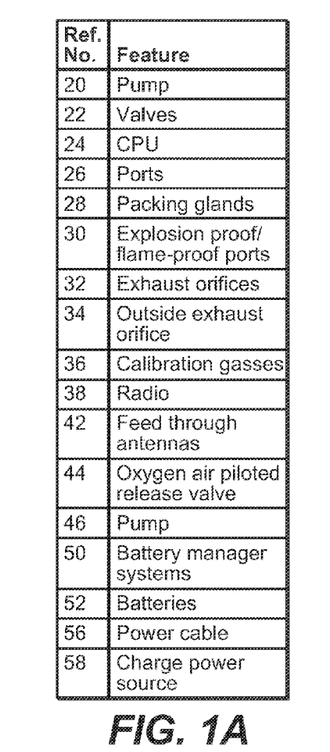
FIG 1A is an appurtenant partial legend identifying boxes having a size insufficient for descriptive labels.

Referring to FIGS. 1 through 8, wherein like reference numerals refer to like components in the various views, there is illustrated therein a new and improved gas monitoring system with oxygen control for human life support in enclosed refuge spaces. FIG. 1 schematically shows the system in its deployed configuration, where it is generally denominated 10 herein.

Referring first to FIGS. 1-3, and initially to the annotated block diagram of FIG. 1, it will be seen that the inventive system includes a battery powered gas monitoring system 12 enclosed in a habitable explosion-proof and flame-proof structure and living space 14, such as a refuge chamber structure shown schematically in FIG. 1. The gas monitoring system includes a sensor system 16 including sensors 17 and a CPU 24. The sensors are provided with air samples from various remote locations fed via air sampling pipes 18 in fluid communication with spaces both outside and inside the refuge chamber 14 by using both suction and exhaust provided by pump 20 and valves 22. All actions of the system are controlled and monitored by the automation intelligence contained in CPU 24.

Air samples are drawn into the system through an input sampling orifices or ports 26 from remote locations as desired. The samples transit through air-tight packing glands 28 and into the sensor system 16 via explosion-proof/flame-proof ports 30 disposed in the base portion 72 of the system enclosure 70 (see also FIGS. 2-3). After being analyzed for gas concentration by sensor subsystem 16, the air samples are exhausted and ejected via explosion-proof/flame-proof ports 30 via valves 22 and thereafter either back to their respective sources inside the chamber via exhaust pipes 19 and exhaust orifices 32 or optionally to the atmosphere outside the chamber via a single outside exhaust orifice 34.

The analysis of gases is performed in an advanced sensor subsystem 16 consisting of electrochemical sensor transducers 17 for carbon monoxide (CO) and oxygen ($O_2$), and non-dispersive infrared transducers for methane ($CH_4$) and carbon dioxide ($CO_2$). The sensor transducer types are selected for low cross sensitivity to other gases, low gas saturation poisoning susceptibility, range, repeatability, and accuracy against a wide variety of systematic and random error sources. Additional or alternative gas sensor transducers for other gases such as nitrogen, hydrogen sulphide, or other gases may also be provided for use within the inventive system, CO, $CO_2$, $CH_4$, and $O_2$ sensors comprising those most suitable for mine refuge chamber monitoring.

Calibrations are performed under automated control of CPU 24 based on the United States Department of Commerce, National Institute of Standards and Testing protocols for a traceable set of calibration gases 36. Calibration steps that involve human interactions, such as attaching calibration gas cuffs and opening calibration gas valves, are communicated and coordinated bi-directionally via wireless radio links to/from the CPU 24 and wireless handsets 40a, 40b, 40c. All measurement results are displayed on wireless handsets 40a-c according to the wireless signals that originate at CPU 24 and as transmitted by radio 38 reaching the wireless handset wirelessly via air-tight wireless feedthroughs/antennas 42. The reciprocal wireless path is used by a human operator to send commands from the wireless handset 40a-c to the CPU 24. Wireless handsets 40a-c are depicted in the diagram as appearing in three locations in and around the refuge chamber structure 14, a first 40a in the airlock 60, a second 40b in the main chamber living quarters 62, and as third 40c outside 64 the chamber. However these devices are truly portable and may be carried or otherwise located for use wherever they are within wireless range of the RF feedthrough antennas 42.

Alerts and alarms and other important messages are sent to wireless handsets 40a-c in addition to the raw data representing the measurements. An automated release of oxygen is accomplished by a control system signal generated by the CPU 24, which acts to open the oxygen air piloted release valve 44 via the air-piloting signal created by pump 46 and sent through air piloting signal line 45, which in turn releases pressured oxygen from oxygen tank 48. The action of this oxygen control system is programmed to maintain the oxygen content of the breathable air within the breathable range of 18.5-23% oxygen by volume.

Intrinsically safe battery manager systems 50 are provided to avoid the possibility of a spark leading to combustion of an inadvertent worst-case atmosphere of hydrogen and/or oxygen and/or methane as might occur through a variety of fault conditions. Small and safe batteries 52 are suitable for use with the inventive system because of the exceptional low-power and high-efficiency design of sensor subsystem 16, which allows 200+ continuous hours of operation of the system on batteries containing too little water to result in a hydrogen out-gassing hazard within the air volume of a typical refuge chamber. Elements 50 and 52 may comprise a single battery manager printed circuit assembly.

The entire inventive system may connect wirelessly to a MineTracer wireless network 54 consisting of as much as a full mine-wide MineTracer system, as described in U.S. Pat. No. 8,294,568, to Barrett, entitled, *Wireless Mine Tracking, Monitoring, and Rescue Communications System*, issued 23 Oct. 2012, and incorporated in its entirety by reference herein. Optionally, it may connect wirelessly to a MineTracer fresh-air subnet controller. Such optional wireless interconnect makes possible bi-directional telemetry and control of the refuge chamber gas monitoring solution via the MineTracer system level user interface located in an above-ground mine office data center. Such capabilities provide additive value to the remote monitoring features already available with MineTracer, which include the tracking/monitoring of individual refuge occupants, the bi-directional text communications to/from refuge occupants, and other sensory monitoring and actuator functions. Alternatively, the entire inventive gas monitoring system may be used in whole or in part as an atmospheric sensing/monitoring system within a MineTracer network without regard to whether it is associated with any refuge chamber.

Many instances of such gas monitoring systems can be deployed within the wireless footprint of a MineTracer wireless network (across an entire mine for example) and used for proactive safety monitoring, accident prevention, or even process control. Electrical connections of the gas monitoring system and (indirectly) to a mine AC power supply are achieved through a power cable 56, which connects the battery manager 50, through an external intrinsically safe charge power source 58.

Figure 2:
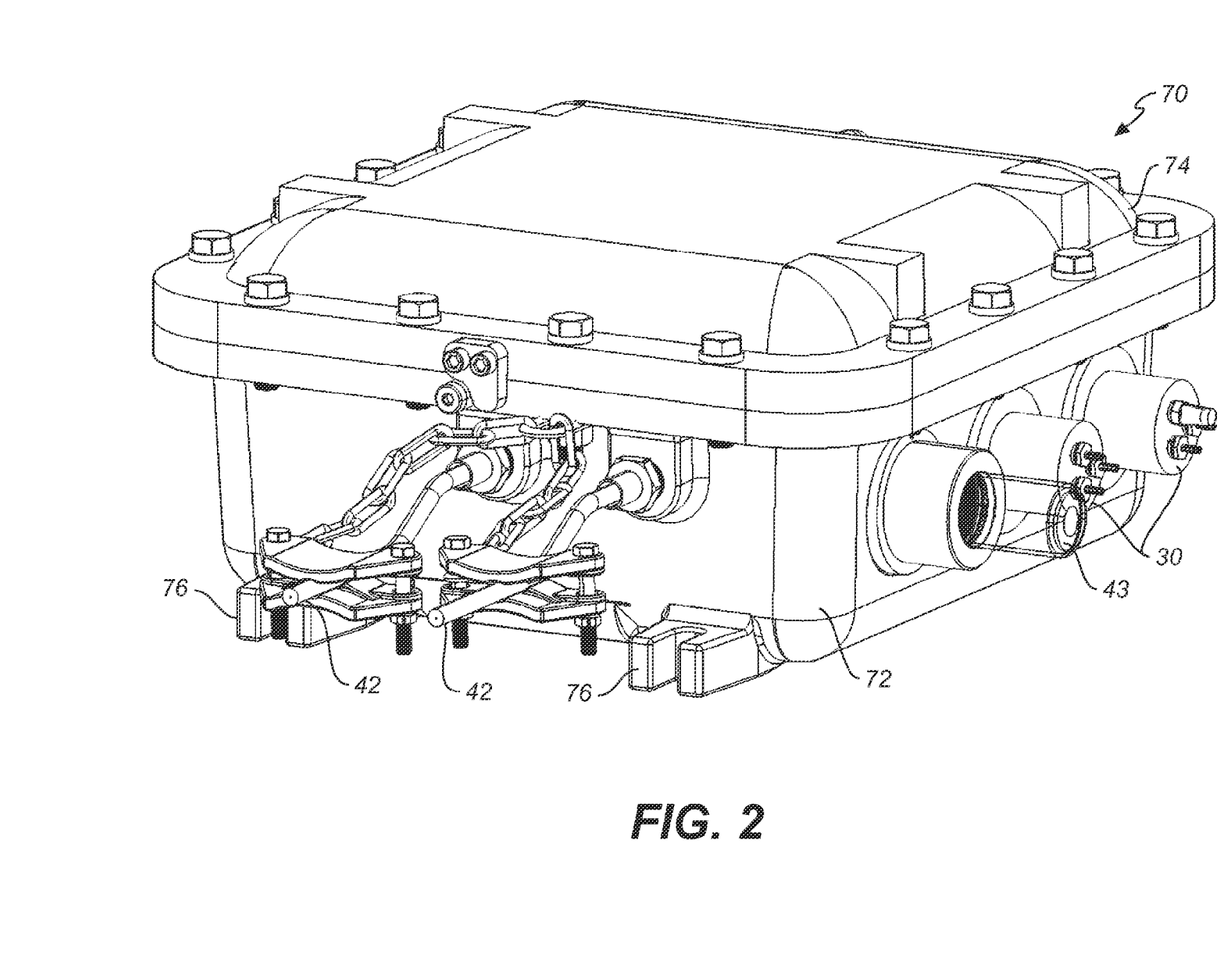
FIG. 2 is an upper perspective view of the explosion-proof and flame-proof enclosure for housing the electrical and pneumatic sensing and control elements of the inventive system.
Figure 3:
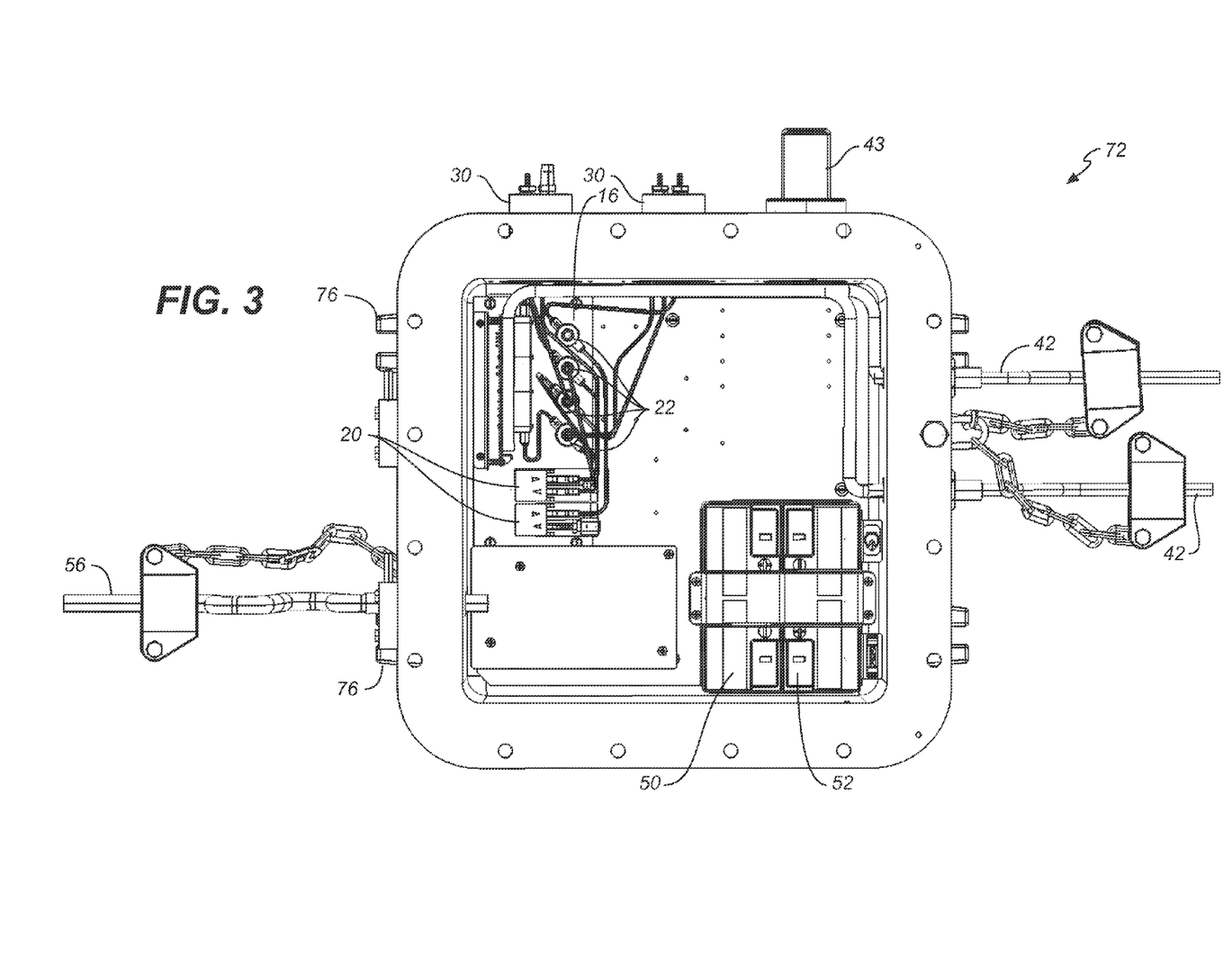
FIG. 3 is a top plan view of the system elements laid out in the base of the enclosure shown in FIG. 2.
Figure 4:
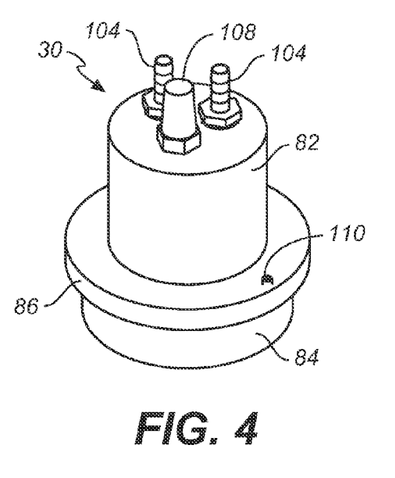
FIG. 4 is an upper perspective view showing the flame-proof port assembly used as a penetration into the enclosure of FIGS. 2-3 to both transmit gases into the sensor/controller system for sampling and to exhaust the gases from the enclosure for discharge to select locations.
Figure 5:
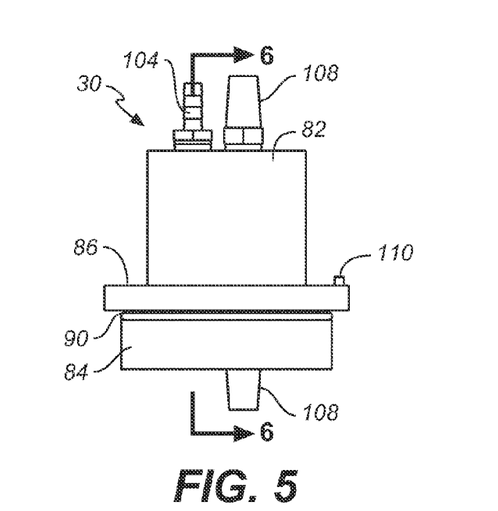
FIG. 5 is a side view in elevation thereof.
Figure 6:
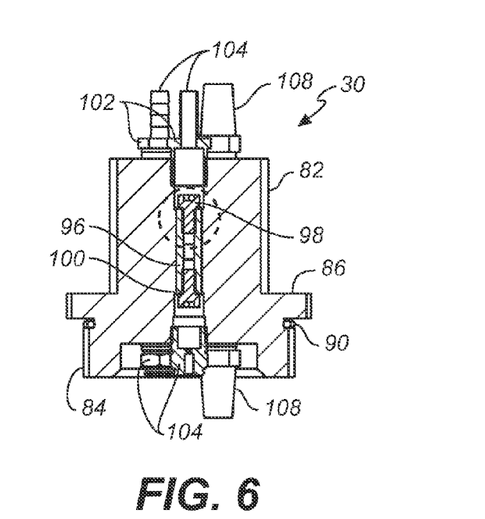
FIG. 6 is a detailed cross-sectional side view in elevation thereof taken along section line 6-6 of FIG. 5.
Figure 7:
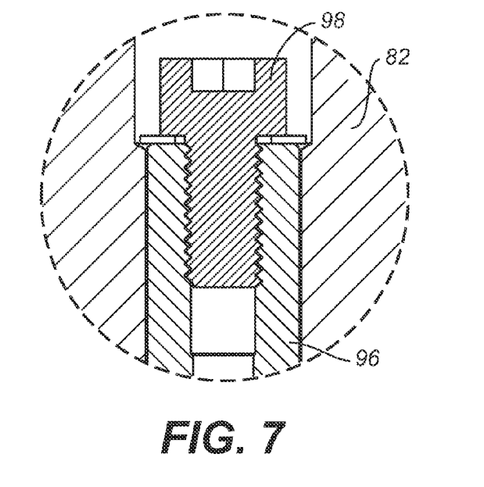
FIG. 7 is a detailed cross-sectional side view in elevation taken along detail section line 7-7 of FIG. 6.
Figure 8:
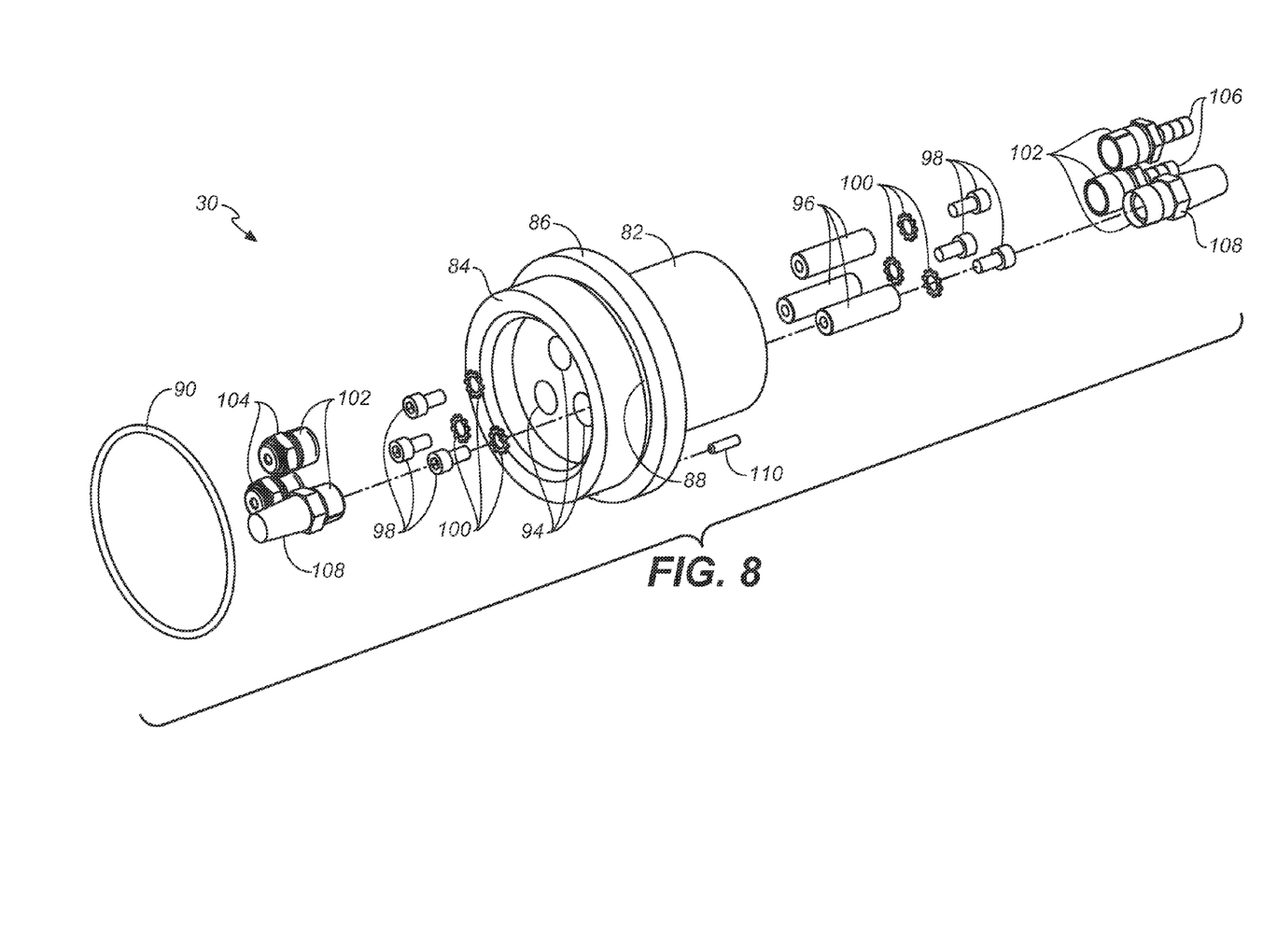
FIG. 8 is an exploded perspective view of the flame-proof port assembly of FIGS. 4-7.

Referring now specifically to FIGS. 2-3, there is shown the explosion-proof and flame-proof enclosure 70, for housing the principle electronic and mechanical components of the battery powered gas monitoring system 12, as shown schematically in FIG. 1. A possible layout and internal configuration for positioning and securing the elements within the enclosure 14 is shown in FIG. 3. The physical enclosure 70 is described in detail in co-pending U.S. patent application Ser. No. 13/484,792, entitled, *Toxic Gas Removal and Air Conditioning System for Human Life Support in Enclosed Refuge Spaces*, which document is incorporated in its entirety by reference herein.

In its most essential aspect, the enclosure 70 includes a base 72, a lid 74, and mounting brackets 76 for securely mounting the enclosure 70 in an appropriate space, such as a mechanical room 64 of the refuge chamber 14. Flame-proof port assemblies 30 are shown disposed in a side of base 72, as is an antenna dome 43 for the RF feedthrough antenna 42 shown in FIG. 1.

Referring next to FIGS. 4-8, there is shown the innovative explosion-proof and flame-proof port assembly 30 employed in the present invention. The assembly is used to selectively permit air samples to be continuously delivered from, and ultimately returned to, atmosphere outside the explosion-proof enclosure 14. As noted above, the air sample are input to the sensor array 16 contained inside the enclosure 70 for gas analysis. The entire assembly is an integral component to an MSHA approved explosion-proof and flame-proof enclosure.

The flame-proof port assembly is a manifold assembly constructed to the United States Department of Labor, Mining Safety and Health Administration ("MHSA") requirements for a "rotating joint" with a solid, dimensioned internal dowel secured with lock washers and screws, so as to allow sampled gas to pass in or out of the port under vacuum or positive pressure supplied by the gas sensor controller pumps and valves, while preventing an internal methane or hydrogen explosion from exiting through the port and into the refuge chamber environment. The flame-proof port is fitted with varying hardware alternatives such as hose barbs, push-on connectors, compression fittings, or gas exhaust mufflers to mate to hardware internal to or external to the gas monitor enclosure.

As seen in FIGS. 4-8, in a preferred embodiment, the flame-proof port assembly 30 includes a generally cylindrical port external portion 82 which extends outside the enclosure 70, and a generally cylindrical insert portion 84 inserted through and captured in the wall of the enclosure base 72. An annular flange 86 is disposed between the external portion and insert portion, at the base of which is an annular channel 88 into which an O-ring 90 is disposed. The external portion 82 terminates at a recess 92 in the insert portion, and includes three through bores 94 into which cylindrical tubular standoffs 96 are disposed and retained at each end by screws 98 and star washers 100.

Push on fittings secured in the port internal portion with sealant 102 (such as sealant tape) may include push on connectors 104, which connect the fittings to valves (element 22 in FIG. 1). External portion connectors may include compression fitting, such as male hose barbs connectors 106, and exhaust mufflers 108, all of which bring the atmosphere outside the enclosure 70 into fluid communication with the sensor system and control system 16 inside the enclosure. Rotation of the port within the enclosure wall is prevented by set screw 110.

Preferably, the system includes two flame-proof ports, though it is physically and structural possible to one or more further ports as needed (for instance, by replacing the RF antenna dome with a third flame-proof air sampling port), if the application requires that gases be sampled from additional locations.

The above disclosure is sufficient to enable one of ordinary skill in the art to practice the invention, and provides the best mode of practicing the invention presently contemplated by the inventor. While there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like.

Therefore, the above description and illustrations should not be construed as limiting the scope of the invention, which is defined by the appended claims.

What is claimed as invention is:

1. A gas monitoring and oxygen supply control system, comprising:
    a flame-proof and explosion proof housing;
    a gas monitoring sensor system enclosed in said housing, said sensor system including a sensor controller, a plurality of gas sensors, and a CPU;
    air sampling pipes in fluid communication with said gas sensors and with the atmospheres to be sampled ;
    input sampling ports disposed on said air sampling pipes and exposed to the atmospheres to be sampled;
    at least one exhaust pipe for venting gases to a select atmosphere outside said housing;
    flame-proof port assemblies disposed through a wall of said housing separating said sensor system from an outside atmosphere and through which said air sampling pipes and said exhaust pipe are disposed;
    at least one pump operatively connected to said air sampling pipes so as to provide both suction and exhaust, said pump electronically connected to and controlled by said CPU;
    a plurality of valves disposed on said air sampling pipes and electronically coupled to and controlled by said CPU;
    a transceiver coupled to said CPU and to a feedthrough radio antenna disposed through a side of said housing for communicating bi-directionally with one or more handsets; and
    an oxygen air piloted release valve in fluid communication with a pressurized oxygen tank, a pneumatic pump in fluid communication with said air piloting release valve through an air piloting signal line, such that said pneumatic pump can send an air-piloting signal to said air piloted release valve to release oxygen from said pressurized oxygen tank, and wherein when said sensor system detects a too low oxygen level, said CPU effects an automated release of oxygen by initiating an instruction to said pneumatic pump to send an air piloting signal to said air piloting release valve, thereby maintaining the oxygen content of the breathable air within a defined space within the breathable range of 18.5-23% oxygen by volume.

2. The gas monitoring and oxygen supply control system of claim 1, wherein said sensor system includes electrochemical sensor transducers or non-dispersive infrared sensor transducers, or a combination of both.

3. The gas monitoring and oxygen supply control system of claim 2, wherein said sensor transducers include at least one carbon monoxide sensor transducer and at least one oxygen sensor transducer.

4. The gas monitoring and oxygen supply control system of claim 2, wherein said sensor transducers include at least one non-dispersive infrared transducer for methane and at least one non-dispersive infrared transducer for carbon dioxide.

5. The gas monitoring and oxygen supply control system of claim 2, wherein said sensor transducers include at least one carbon monoxide sensor transducer, at least one oxygen sensor transducer, at least one non-dispersive infrared transducer for methane, and at least one non-dispersive infrared transducer for carbon dioxide.

6. The gas monitoring and oxygen supply control system of claim 2, wherein said sensor transducers include sensor transducers for nitrogen.

7. The gas monitoring and oxygen supply control system of claim 2, wherein said sensor transducers include sensor transducers for hydrogen sulphide.

8. The gas monitoring and oxygen supply control system of claim 1, wherein system calibrations are performed under automated control of said CPU.

9. The gas monitoring and oxygen supply control system of claim 8, wherein calibration steps involving human actions are communicated and coordinated bi-directionally via wireless radio links to and from said CPU using one or more wireless handsets.

10. The gas monitoring and oxygen supply control system of claim 9, wherein measurement results from said sensor system are displayed on said wireless handsets, and further including a reciprocal wireless path for use by a human operator to send commands from said wireless handsets to said CPU.

11. The gas monitoring and oxygen supply control system of claim 10, wherein alerts and alarms and other important messages are sent to said wireless handsets from said CPU.

12. The gas monitoring and oxygen supply control system of claim 1, further including an intrinsically safe battery manager system for operating said system in the event of power failure from an external electrical power supply.

13. The gas monitoring and oxygen supply control system of claim 1, wherein said system is wirelessly connected to a wireless mine tracking, monitoring, and rescue communications system.

14. The gas monitoring and oxygen supply control system of claim 1, wherein said system includes a first flame-proof port assembly for air intake and a second for at least one exhaust element.

15. The gas monitoring and oxygen supply control system of claim 1, wherein said air sampling pipes are in fluid communication with spaces both outside and inside a refuge chamber.

16. A gas monitoring and oxygen supply control system, comprising:
a flame-proof and explosion proof housing;
a gas monitoring sensor system enclosed in said housing, said sensor system including a sensor controller, a plurality of gas sensors, and a CPU;
air sampling pipes in fluid communication with said gas sensors and with the atmospheres to be sampled;
input sampling ports disposed on said air sampling pipes and exposed to the atmospheres to be sampled;
at least one exhaust pipe for venting gases to a select atmosphere outside said housing;
flame-proof port assemblies disposed through a wall of said housing separating said sensor system from an outside atmosphere and through which said air sampling pipes and said exhaust pipe are disposed;
at least one pump operatively connected to said air sampling pipes so as to provide both suction and exhaust, said pump electronically connected to and controlled by said CPU;
a plurality of valves disposed on said air sampling pipes and electronically coupled to and controlled by said CPU; and
transceiver coupled to said CPU and to a feedthrough radio antenna disposed through a side of said housing for communicating bi-directionally with one or more handsets;
wherein each of said flame-proof port assemblies comprises a generally cylindrical port external portion extending outside of said housing, a generally cylindrical insert portion inserted through and captured in a wall of said housing, an annular flange disposed between said external portion and said insert portion, a plurality of bore holes extending through said external and said internal portions, and fittings disposed in each of said bore holes for connecting tubes, pipes, or other conduits through which gases may be conveyed.

17. The gas monitoring and oxygen supply control system of claim 16, wherein said system includes two flame-proof port assemblies.

18. The gas monitoring and oxygen supply control system of claim 16, wherein said fittings include at least one exhaust muffler.

19. The gas monitoring and oxygen supply control system of claim 16, wherein air samples are drawn into said gas monitoring and oxygen supply control system through said input sampling ports from remote locations are passed into said sensor system, are analyzed by said sensor system for gas concentration, and are exhausted and ejected from said housing via said flame-proof port assemblies and said valves, and thereafter to a selected atmosphere via at least one exhaust orifice.

* * * * *